United States Patent [19]

Shepherd

[11] Patent Number: 5,454,379
[45] Date of Patent: Oct. 3, 1995

[54] DEVICE FOR SHIELDING THE MALE ORGAN

[76] Inventor: William G. Shepherd, 155 Northampton Rd., Amherst, Mass. 01002

[21] Appl. No.: 303,508

[22] Filed: Sep. 9, 1994

[51] Int. Cl.$^6$ .................................................. A61F 6/02
[52] U.S. Cl. ........................... 128/842; 128/844; 128/918
[58] Field of Search .................................. 128/842, 844, 128/918; 604/347–353

[56] References Cited

U.S. PATENT DOCUMENTS

| | | | |
|---|---|---|---|
| D. 254,808 | 4/1980 | Meldahl | D24/99 |
| 2,604,092 | 7/1952 | Brown et al. | 128/132 |
| 3,128,762 | 4/1964 | Young | 128/844 |
| 3,648,700 | 3/1972 | Warner | 128/294 |
| 4,187,851 | 2/1980 | Hause | 128/295 |
| 4,475,910 | 10/1984 | Conway et al. | 604/352 |
| 4,638,790 | 1/1987 | Conway et al. | 128/138 R |
| 4,735,621 | 4/1988 | Hessel | 604/349 |
| 4,769,020 | 9/1988 | Eaton | 604/352 |
| 4,798,600 | 1/1989 | Meadows | 128/844 |
| 4,805,604 | 2/1989 | Spery | 128/79 |
| 4,817,593 | 4/1989 | Taller | 128/844 |
| 4,869,723 | 9/1989 | Harmon | 604/349 |
| 4,920,983 | 5/1990 | Jimenez | 128/844 |
| 4,966,166 | 10/1990 | Leffler | 128/844 |
| 5,050,619 | 9/1991 | Ferguson | 128/844 |
| 5,121,755 | 6/1992 | Hegedusch | 128/918 |
| 5,137,032 | 8/1992 | Harmon | 128/844 |
| 5,199,444 | 4/1993 | Wheeler | 128/844 |
| 5,327,911 | 7/1994 | Pien | 128/844 |
| 5,351,699 | 10/1994 | Hammons | 128/918 |

*Primary Examiner*—Michael A. Brown
*Attorney, Agent, or Firm*—Hamilton, Brook, Smith & Reynolds

[57] ABSTRACT

A device for shielding the male organ includes a tube having a closed end and an open end which forms a cavity for receiving the male organ through the open end. The device further includes an impermeable membrane which is essentially cylindrical in shape having a proximal end and a distal end, wherein the distal end is circumferentially attached about the open end of the tube and wherein the proximal end has means for securing the membrane to the base of the male organ.

16 Claims, 4 Drawing Sheets

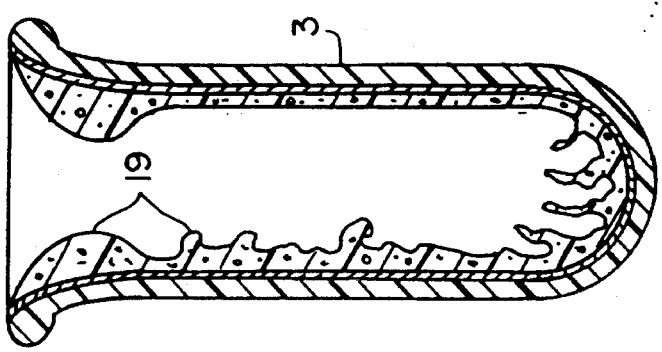
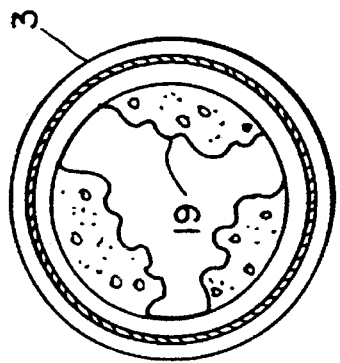
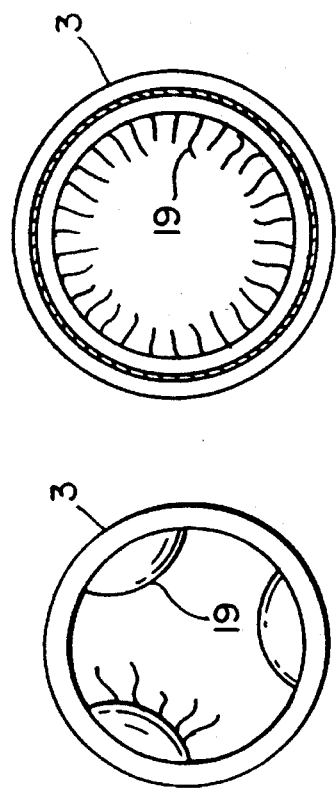
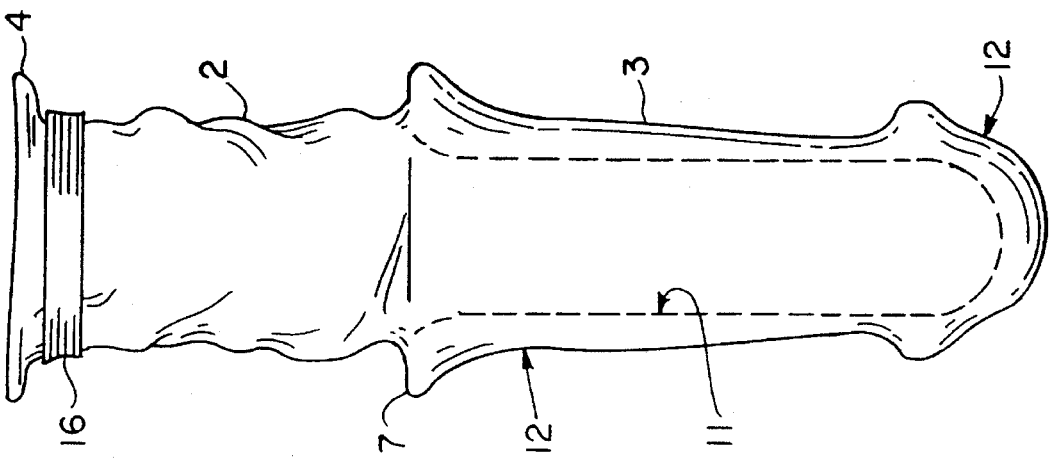
FIG. 7D
FIG. 7B
FIG. 7C
FIG. 7A
FIG. 6

DEVICE FOR SHIELDING THE MALE ORGAN

BACKGROUND OF THE INVENTION

In order to gain satisfactory sexual activity, there are two main desires, stimulation of the sexual organs or at least of one partner's organ, and security against transmission of disease or when contraception is desired of sperm.

The standard physical device to provide protection against disease conception or both is the male condom, a thin membrane which is rolled tightly over the male organ. Its major disadvantage is that it largely or entirely prevents friction for the male user, thereby reducing or eliminating the stimulation of sexual activity. The condom is also awkward in use, being difficult to place on the organ and subject to slipping off.

Because condoms are unsatisfactory to male users, there is a reluctance to use them. Consequently, the rates of venereal and AIDS infection, and the rates of unwanted pregnancies, are increased.

As a further disadvantage, condoms are a simple, uniform, and utilitarian device. Yet human sexual activities involve an extremely wide variety of personal situations for sex, of purposes and interests in sex, of degrees of concern about the risk of disease or conception, of types of sexual activity, for instance, heterosexual intercourse, manual play, oral stimulation, self-stimulation, etc., and of partners' ages and preferences.

Efforts to improve the condom have mainly tried to make it become even more insignificant, especially with ever-thinner membranes. There have been some efforts to enlarge the tip of some condoms to provide some looseness and to alter the surfaces. But those have accomplished little so far, and they have raised the risks of the condom's falling off during use.

"Sex toys," which can simulate some features of the male organ, often in exaggerated forms, include a variety of vibrators, with simple cylindrical, tapered or male-organ-simulating shapes to be inserted into the female. Such vibrators lack the enclosure for the actual male organ, the ability to insert the male's own organ fully into the female, and the mutual stimulating process.

Another category is hollow fake male organs, often worn with harnesses. They are usually designed for penetration, often with an exaggerated exterior size. They are usually made of stiff materials. Particularly, they do not provide for a sliding and friction of the male organ inside the hollow simulated organ. Also, they are not lined or otherwise prepared for stimulation of either partner. Some versions of them are called Prosthetic Penis Aids (PPAs). They too are fixed over the male's organ, often with a harness, thereby preventing any sliding and stimulation for the male.

Still another category is various pumps and related mechanical devices, which a male can use to cause friction or pulsing for his organ. But these pumps are large and unwieldy, with no possibility of being used for mutual intimate activity in the manner of the invention.

Finally, there are "extenders" or "extensions," which fasten an elongated molded rubber tip of a simulated male organ onto the real organ, seeking to make it seem longer. One version even contains a vibrating device. These extenders are tightly rolled onto the male organ. There is no enclosure of the entire organ. There can be no sliding of the male organ inside the extension. There is no anchoring to the base of the real organ, and the extension does not provide for secure protection.

Therefore, a need exists for an improved apparatus that causes sexual stimulation for both partners during sexual activity is securely anchored without preventing friction; comes in varied shapes, sizes, and surfaces, in order to fit human diversity in anatomical sizes and personal interests; and provides protection.

SUMMARY OF THE INVENTION

The present invention relates to a device that is a shield for the male organ. The device includes a tube having a closed end and an open end, which forms a cavity for received the male organ through the open end. The device further includes an impermeable membrane, which is essentially cylindrical in shape having a proximal end and a distal end, wherein it is circumferentially attached about the open end of the tube and wherein the proximal end has means for securing the membrane to the base of the male organ.

The invention is designed to contain the enlarged male organ within an enclosed structure, which can also be soft-surfaced, freely-moving and stimulating. The male organ moves freely within this enclosure during manual sexual activity or intercourse. It also simultaneously provides the female partner with the experience of an inserted, moving, and stimulating male organ. It does this by the use of simple, normal sexual motions, rather than by artificial postures, mechanisms, or manipulation. The device therefore becomes integral to intimate, joint sexual activity, providing satisfaction to both partners during intercourse. It can also be used for manual stimulation of the male organ and for self-stimulation by the male.

BRIEF DESCRIPTION OF THE DRAWINGS

FIG. 6 shows a side view of another embodiment of the invention having a structured exterior.

FIGS. 7A, 7B, 7C and 7D show cross-sectional views of embodiments of the interior of the tube of the invention.

DETAILED DESCRIPTION OF THE INVENTION

The features and other details of the method and apparatus of the invention will now be more particularly described with reference to the accompanying drawings and pointed out in the claims. The same numeral present in different figures represents the same item. It will be understood that the particular embodiments of the invention are shown by way of illustration and not as limitations of the invention. The principal features of this invention can be employed in various embodiments without departing from the scope of the invention.

The invention has a structure which has two main parts, an impermeable membrane portion that is relatively thin and flexible, and a closed-end tube or sleeve. The total length of the device, the membrane plus the tube, while extended is substantially greater than that of the extended male organ which it encloses, up to approximately twice the length or more.

The membrane serves as a loose-fitting but tightly-anchored holder, which allows the tube to slide along and around the male organ. The membrane portion is thin, loose and impermeable. It has at least two embodiments, a connector and a larger, complete enclosure.

In one embodiment, the membrane connects the tube to the base of the male user's organ. It is essentially cylindrical in shape, but it is highly flexible and large enough to let the male organ slip loosely within it and, possibly, to serve as a reservoir to hold excess air. The length of the membrane can vary from one or two inches up to nearly, but not equal to or longer than the length of the extended organ. In this embodiment, the membrane is prepared separately and is then joined by fusion or adhesion to the tube during formation.

Figure 2:
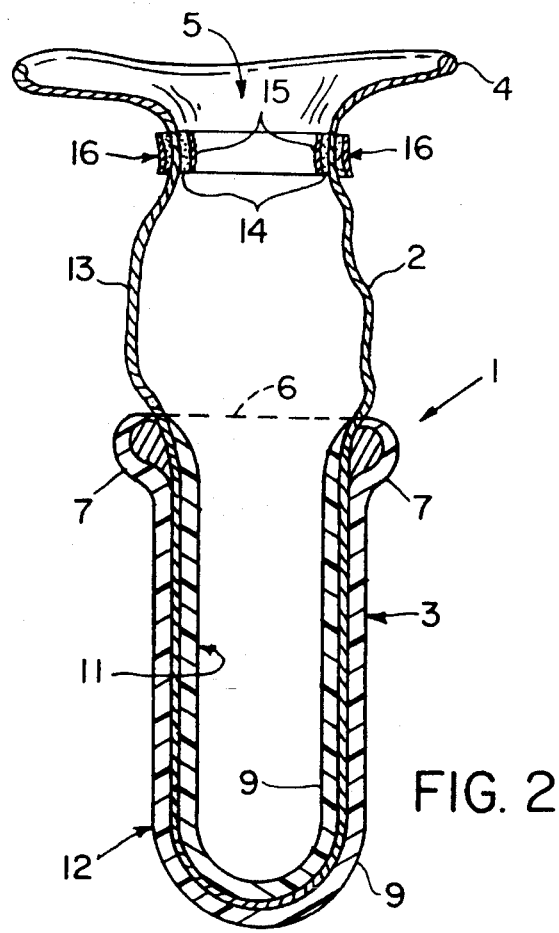
FIG. 2 shows a cross-sectional view of a second embodiment of the invention in which the distal end of the membrane forms a liner embedded within the tube.

In another embodiment, an effective approach is to have a single large fabric closed-end tube serve as both the membrane and the core of the tube, as shown in FIG. 2. The tube is created by dipping the tube of the membrane into spongy material, such as polyurethane, which adheres to the membrane and hardens into the desired thickness and consistency. The ability of the device to be everted makes it possible to create the body and surfaces of the tube by successively dipping the inside, but everted, surface and then after turning the device back to its final position dipping the outside surface so as to obtain another substantial layer of material. In addition, the flange around the opening of the tube may be created by applying a thick adhering ring around the device before the outside surface is dipped.

Figure 3:
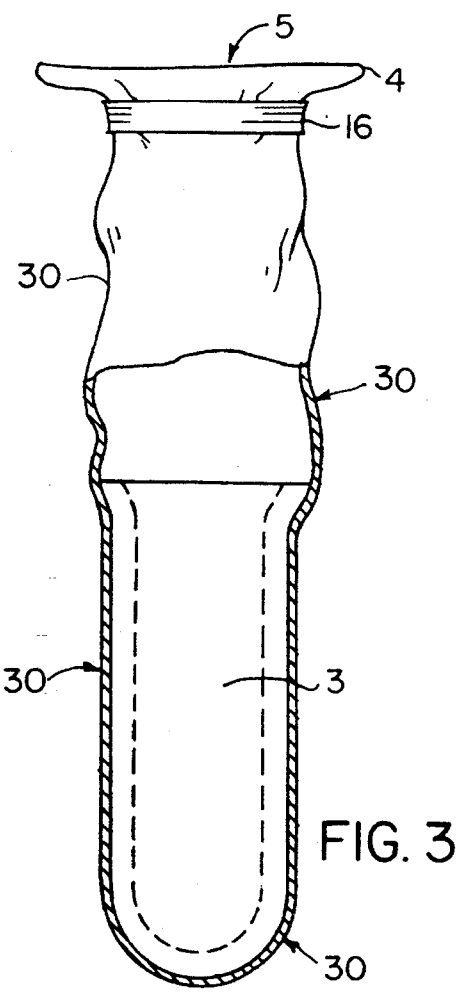
FIG. 3 shows a cross-sectional view of a third embodiment of the invention in which the distal end of the membrane forms a liner on the outer surface of the tube.

Alternatively, as shown in FIG. 3, the membrane may be part of a longer, looser, thin-walled, sleeve-like closed-end tube, which is large enough to surround and contain a wholly separate tube, rather than to connect with it. The membrane can then be physically separated from the tube, in storage and possibly use. However, the outside membrane can be fastened to the tube by applying an internal or external tape to the membrane. During the invention'use for intercourse, the membrane of the device is anchored to the base of the male organ by a narrow strip or strips of adhesive.

Versions of the membrane may be made of any flexible, impermeable membrane or cloth-like material, such as a polymer or treated natural material. The membrane may instead be elastic, in some degree, if users desire and made from a material typically used for condoms.

The tube is usually a moderately soft, lightweight and well-fitted container for the entire male organ. This portion is like a closed-end tube with relatively thick and soft sides and a rounded tip. This tube or sleeve is not elastic, though it is soft and usually easily bendable, and the thickness of its walls may vary from about 0.125 to 0.5 inches. Because it is not stretchable, this container needs to be reasonably well fitted in size to the specific user's extended organ. But the fit is loose, so as to permit free movement and friction.

This fit makes it possible for the tube to serve its primary purpose to provide well-adjusted stimulation to the enclosed organ as it slides freely inside the tube. The tube is lined internally with one or more stimulating surfaces or attachments or both. Its external surface may be plain, provided with stimulating surface patterns or attachments or both, or shaped with anatomical features or a combination thereof.

As a matter of length, the interior of the tube portion is a little longer than the length of the entire extended organ. The exterior of the tube may range from slightly longer to much longer than the extended male organ.

As for weight, the tube can be lightweight, as little as about a half ounce or possibly as much as three ounces. The actual weight depends on the specific variations in size, structure, composition, methods of production, and possible attachments.

The tube can have many possible variations of sizes, length and circumference, thickness of walls, degrees of softness or firmness, interior and exterior shapes, surfaces and attachments, colors and other decorations. It may have the single membrane embedded within its thickness.

The stimulating surfaces or attachments or both on the interior and exterior surfaces may be preinstalled on the device, or they may be applied to the device by the user at some time before the device is employed.

The device may be used in its produced form, with complex shapes and stimulating attachments already included. Alternatively, before sexual activity, the user may prepare the inner or outer or both surfaces by applying specific stimulating features.

The device can be provided in a small, flat stiff-paper envelope or packet, intended to be as small, portable, and convenient to open as possible. The device can be folded, with the tube usually folded once transversely across its middle. The packet can then usually be less than about four inches long, three inches wide, and 0.5 to 0.625 inches thick. The packet may also contain attachments for the device. Alternatively, the attachments may be obtained in a separate packet.

Both parts of the device can easily be everted. That allows the user to adapt and prepare the inner surfaces. The possible attachments have a prestick surface so that they can be easily lifted from their holder and pressed onto the device in any desired pattern and frequency. The outside surface may also be similarly prepared.

Once the device is prepared for use, and with lubricants inserted as desired, it is placed or draped gently over the extended male organ. It is not rolled tightly down, as with a condom. Excess air is gently expelled, by squeezing the device in a stripping motion from tip to base. The neck of the membrane is fastened around the male organ's base, using one or more narrow strips of adhesive on the inside or outside or both of the neck of the membrane. Note that the adhesive fastenings need not be used if the sexual activity is manual stimulation of the male organ. In fact, a simpler and cheaper manual-play version of the invention may be produced and used, with no adhesive properties.

Whether it is fastened or not, the device is available for extended manual play, by being slid up and down the organ or with twisting strokes or both.

For intercourse, the tube is slid down fully over the male organ, and then the device-covered organ is introduced into the female's vagina. The male is then free to adopt a piston-like motion within the tube providing stimulation to his organ. But the male can also provide stimulation to his partner by his actions. By withdrawing his organ out further, the male uses the anchored membrane of the device to pull the tube of the device partly or nearly entirely out of the female's vagina. Then by sliding his organ back into the tube and continuing the motion, the male causes the tube to slide fully back into the female. That causes the tube to stimulate the female partner as it slides in, as occurs during normal intercourse.

In the process, the device provides both partners with the repetitive to-and-fro motion and friction that are characteristic of unencumbered sexual intercourse. In addition, the stimulation for both partners may be enhanced by the special surfaces or attachments or both that are on both the inner and outer surfaces of the device. Lubricants can also be freely used as preferred, both inside and outside the device. In fact, partners can usually experiment with interior and exterior lubricants, so as to obtain the best balance between them. That allows them to get the best combination of sliding motions of the device.

The membrane is a thin, impermeable, flexible, but not necessarily elastic sleeve, either as a connector or an enclosing sleeve. It may be a polymer cloth or other fabric-like material, or it may be elastic, and large enough to be free-sliding along the male organ, or even very loosely draped, firmly anchored to the base of the male organ by a strip or strips of tape, and provided with a collar at the opening.

The tube is a soft and lightweight closed-end tube, of spongy materials, usually capable of being everted, lined or able to be lined with stimulating surfaces and anatomically-simulating devices, on the inside and the outside surfaces, usually provided with a flange at its opening, and sized to fit specifically over the male user's organ in a gentle fashion so that stimulation is promoted by sliding.

Not only does the device provide for active and repetitive stimulation for both partners. It also permits a wide diversity of variations in size, shape and stimulating methods, which provide sensations in excess of what unprotected sex would create. The female may perceive a larger or anatomically different male organ, thanks to the size and shape of the tube. The male may perceive a tighter or differently textured vagina, from the shape and lining of the inside of the tube. Alternatively, the inner and outer conditions of the device may be varied in other ways. Therefore, both partners are able to vary their sexual experience, by using different versions of the device.

Moreover, both partners participate and remain in control during the mutual sexual activity. The male manages the depth, rate and frequency of his insertions and withdrawals. The female also participates by her pelvic motions, as in normal unfettered intercourse. Alternatively, during foreplay, she can accomplish extensive manual stimulation of the male organ using the device, if she wishes to have a shorter interval of intercourse activity.

The invention also insulates the two partners from disease and conception. But that is only a secondary result of the device. The invention is designed to be integral to the partners' joint sexual activity, under a wide variety of conditions. It is to be candidly and skillfully used for stimulation, but with much the same motions that are used during normal intercourse. Alternatively, it can be used effectively for manual stimulation of the male organ. It is not intended to be so thin, plain and insignificant that it is not noticed, as compared with a standard condom.

The device is designed to allow the male organ to move freely and vigorously inside them. Friction for the enclosed male organ is provided by means of interior surfaces and shapes that can be specifically arranged by the user in any desired degree and patterns. The elements to be added may simulate inner conditions of a female's sexually active parts.

Some versions may have anatomically appropriate folds and sliding surfaces on the inside of the device. There may be pads, transverse or longitudinal, on either the interior or exterior or both. The linings may also include patches, rings or lines of hair-like strands. Such strands may be short, medium or long up to about one and half inches or even longer, and of varying degrees of coarseness and curliness. The linings and attachments may also be applied to the exterior surface either of the tube or of the membrane. These specially prepared shapes and surfaces may vary by locations in the devices, in order to provide the variety of sensations and stimulations that are experienced during intercourse, oral activity, or manual activity.

The walls of the tube are thick enough to have structure, body and possibly details of shape. Although a standard version may have walls of approximately 0.25 to 0.375 inches, the thickness may be less or greater, either throughout the tube or merely at specific parts of the device, depending on the preferences of the partners.

The tube may usually may be made of flexible materials such as one or more layers or areas of spongy substances, such as lightweight rubber, polymers, or similar materials, etc. That consistency provides for a preferred degree of softness or stiffness, and the ability to evert the tube for preparing both surfaces. The surfaces may be relatively porous or smooth, silky or roughened.

The substances themselves provide an impermeable barrier. Alternatively, a barrier membrane may be imbedded in the soft, spongy wall, both for impermeability and for extra strength against tearing.

The device may either be preshaped and prelined, or instead provided in a plain shape that can be altered by the user. The total length of the device may vary, up to or exceeding twice the length of the extended male organ. The tube has an interior space longer than the user's extended organ, to allow for free movement. The circumference, thickness and degree of firmness may also vary, depending on the users' preferences.

The device need not be symmetrical or uniform, either externally or internally. For example, there may be preinstalled pads or other forms of stimulation along one side of the inner surface, but not extending all the way around the inner surface. Either in production or in final adjustments by the user, the special stimulating surfaces or attachments or both can be placed in any parts of the interior, in patches, rings, lines, spirals, or other forms. Alternatively, there may be a vibrating ability which is placed along one side of the device, or at the tip or both.

In addition, by production or users' preparation, the device may have an external shape which provides to the female partner the experience of a larger or differently shaped male organ. Alternatively, the device may emphasize only thickness or only length. Also, the device may have unusual external shapes, such as a large corona or other ridges, to fit the possible interests and preferences of the partner.

The invention is of light weight, in order not to interfere with the desired activity and perceptions. This lightness is obtained by the use of foamy or spongy materials, composed of various alternative polymers, to form the body of the tube. For instance, a polyurethane is suitable. Also, the membrane is comprised of cloth-like or elastic materials, which are also very light in weight. Any stimulating attachments and adhesive attaching strips are also of minimal weight.

The degree of stiffness, softness and flexibility of both portions of the device may vary. The degree of softness may be affected by the nature of the materials or by the thickness of the walls or by both. Some users may prefer relatively stiff versions, while others favor soft and pliable ones.

An important part of the invention is the very secure anchoring of the device by adhesion at the base of the male organ. That is what permits a pulling out and plunging in of the tube, so that the female partner experiences friction along with the male partner. The device usually is attached by a narrow adhesive strip at the base of the male organ See U.S. Pat. application Ser. No. 08/259,602, filed Jun. 14, 1994. The teachings of which are incorporated herein by reference. One such strip may be preapplied to the inside of the neck of the device. Other strips may be applied separately to the base of the male organ, a double-sided adhesive band, which then sticks to the preapplied inner strip, or may be wrapped around the neck of the device on the outside or both.

Alternative methods for fastening may be also used, such as using Velcro™ brand hook and pile fasteners in place of the external strip or tabs. Also, some versions of the device may be designed to be used while they are placed over the male organ but are not actually anchored to the male. An important type of such unattached use would be in order to facilitate manual sex activity or masturbation.

The device must deal with the problem of air. During use, excess air inside the invention may cause bulging of the device. Alternatively, it may escape, causing unexpected and awkward noises and possibly loosening the adhesive attachment. If the tube is quite soft, entrapped air is a minor problem. Air may be eliminated from inside the device before it is attached. The user merely squeezes out the air after the organ is inserted fully into the tube. The reciprocal motion of the male organ then creates no internal air displacement and flow. When the male organ is withdrawn from the tube, the walls of the tube are collapsed together, because they are so soft. Reinsertion of the male organ then enlarges the tube without the occurrence of any air flows.

Alternatively, the tube may be somewhat stiffer, enough so that it retains its structural shape and does not collapse during the withdrawal of the male organ. Then air must somehow flow into the tube, if the male organ is to slide out of it during the withdrawal phase, otherwise, the male organ cannot slide and it experience no friction inside the device.

For air to flow, the tube must have some kind of channel or groove in the internal shape of the tube. That requires a proper design of the tube, which may involve one or more grooves. The grooves could be provided by placing the interior of the tube over a suitable molding device. Such grooves can of course be consistent with a stimulating internal surface.

The out-flowing air from the tube during insertion of the organ is contained in the loose volume of the membrane. That loose portion would bulge significantly during this phase, but that need not interfere with the functioning of the device. The bulging simply occurs outside the female's body, and no pressure need occur which might force air noisily through the adhesive attachment. In fact, the extra pressure of the air bulge around the male pubic area, and around the female's vulva, may provide for added stimulation.

Color and decoration can be an integral element of the invention. Unlike the condom, which is minimal and of essentially one color, tan rubber, the invention is designed to be noticed, adapted and used. Also the nature of the invention permits and encourages the use of interesting colors and decorations, for those users who do not wish the invention to mimic flesh tones. The use of colors and decorations can introduce elements of style and humor, which support and encourage a good experience of sex activity. The use of color ranges from restrained and tasteful up to bright and entertaining. Color might not seem to be a distinctive feature, but it can be. The invention provides a new and more open form of protecting sexual activity, and the use of color and decorations can be integral to the style, humor and variety of this distinctive experience.

The membranous cloth for embodiments can be produced by impermeable polymer cloth production methods, as are known in the art, which create tubular sleeves with one or two open ends. The inner and outer surfaces may be selected with specific properties of smoothness, roughness, etc.

The drawings represent only a few examples among the diversity of possible shapes, surfaces, thicknesses, degrees of softness, degrees of flexibility, stimulating surfaces, attachments and other possible mechanisms, colors and decorations, and methods of attachment. Other variations are possible.

Figure 1:
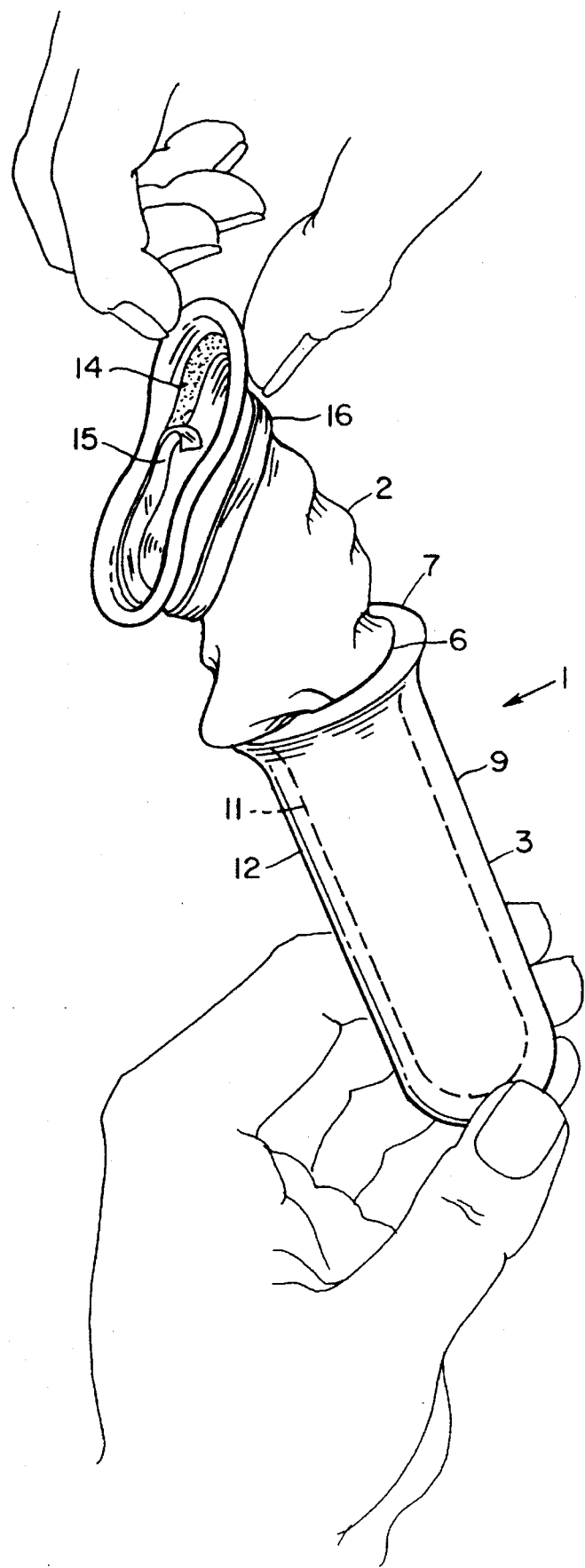
FIG. 1 shows a perspective view of one embodiment of this invention in a hand-held position prior to application.

FIG. 1 shows an embodiment of the device as it is removed from its container and is held ready to be prepared for use. Notice in FIG. 1 that the device is not rolled up before use, in contrast to standard condoms. The membrane is loose and flexible, and it has a collar extending outward from the neck opening. The collar is used to grasp the device gently during insertion of any lubricant and then to place the device over the male organ.

FIG. 1 depicts device 1 with membrane 2 and tube 3. There is a collar 4 at the opening 5 of membrane 2. Membrane 2 is large enough to slide or drape easily over the extended male organ 8. Tube 3 has a neck opening 6 with a flange 7. Tube 3 is shown in a plain version, with unshaped walls 9 that are soft on both the interior 11 and exterior 12 surfaces. Membrane 2 is a thin, loose, impermeable, non-elastic, membrane 13.

A narrow strip of adhesive 14 is preapplied to the inside of the neck 5 of membrane 2, and that adhesive 14 is covered by removable paper strip 15. There is also a preattached, covered adhesive tape 16 around the outside of the neck 5, in this version.

Tube 3 has moderate flange 7 at its opening 6, so that the male's body 17 can press the tube forward into the female's vagina 18. The inner 11 and outer 12 surfaces of tube 3 have the softness and consistency of skin, and they are also ready to have specific stimulating surfaces and attachments 19 applied securely to them if the partners wish.

FIG. 2 shows an other embodiment, in a cross-sectional view of device 1, with a single membrane used for membrane 2 and the core of tube 3.

FIG. 3 shows another embodiment of the invention. The tube is enclosed in the large, long enclosing sleeve. The sleeve has the same adhesive elements at its neck as the embodiment in FIG. 1. The sleeve can also be prepared with the same external stimulating attachments that, in as the embodiment in FIG. 1, are on the outside of the tube. Tube 3 is enclosed in sleeve 30. The sleeve 30 can also be prepared with the same external stimulating attachments 19 that, in Version 1, go on the outside 12 of tube 3. Moreover, the enclosing sleeve 30 can be attached by the user to tube 3 with adhesive from the kit, if that is wished in order to provide for greater control or security.

Figure 4:
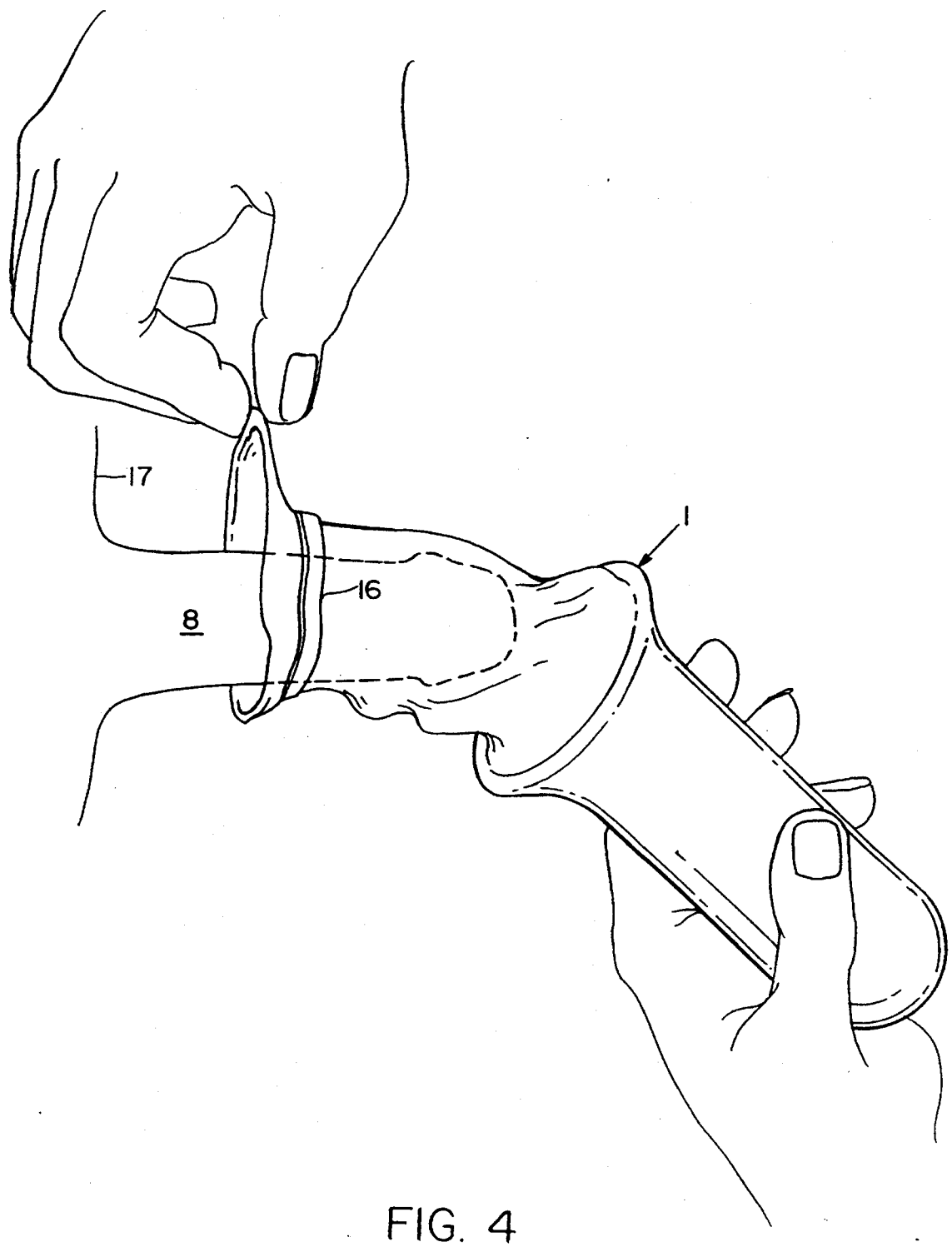
FIG. 4 shows a perspective semi-diagrammatic view of the invention in relation to the typical relative size of a male organ.

In FIG. 4, device 1 is being placed over the male organ 8 by either partner or both.

Figure 5:
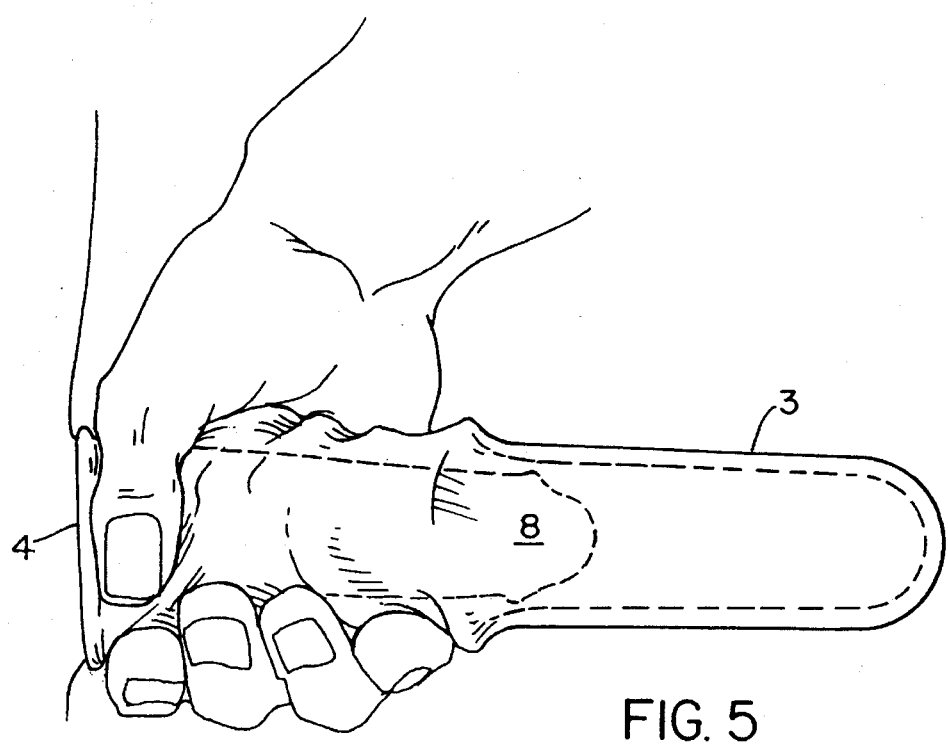
FIG. 5 shows a perspective view of the invention as it is being fastened to the base of the male organ.

In FIG. 5, device 1 is being fastened to the base of organ

8. The covering tape inside the neck is removed, the remaining air been squeezed from inside the device, and the neck of the device is firmly squeezed around the base of the organ. The preinstalled outside tape is then exposed and wrapped tightly around the neck 5 of membrane, giving a double layer of attachment. The device is ready for use in manual stimulation or intercourse.

The organ, covered by the device, is inserted in the partner's vagina. The membrane of the device is compressed accordion-like between the male's and female's bodies. Alternatively, it might bulge slightly with air from inside the tube. The organ is then withdrawn far enough to pull the tube of the invention nearly out of the vagina. The device can now be reinserted by a forward movement of the male organ 8.

FIG. 6 shows a version of the invention 1 whose tube 3 has an anatomically shaped form 9, in this embodiment, somewhat exaggerated and fanciful. Alternatively, a simple tube 3 could be modified by the user by applying attachments 19, in order to give a complex, unusual shape 9.

FIGS. 7A, 7B, 7C and 7D show cross-sectional views of an alternative tube 3, which have various thicknesses, shapes and attachments 19. In FIG. 7A, there are longitudinal pads, including one with attached hairs. FIG. 7B involves a ring of attached hairs. In FIG. 7C, several soft irregular lip-like attachments have been applied. In the longitudinal cross-sectional views of FIG. 7D, there are pads near the opening, plus a strip of soft, lip-like protrusions.

Equivalents

Those skilled in the art will recognize, or be able to ascertain using no more than routine experimentation, many equivalents to the specific embodiments of the invention described specifically herein. Such equivalents are intended to be encompassed in the scope of the claims.

I claim:

1. A device for shielding the male organ, comprising:
   a) a structured tubular section having a side wall, a closed end and an open end, which forms a cavity for receiving the male organ through said open end; and
   b) an impermeable membranous section having a membrane, which has a wall thickness that is less than the thickness of the side wall of the tubular section and is essentially cylindrical in shape having a proximal end and a distal end, wherein said distal end is circumferentially attached about the open end of said tubular section and wherein said proximal end has means for securing said membrane to the base of the male organ.

2. The device of claim 1 wherein said means for securing is adjustable.

3. The device of claim 1 wherein said tubular section is formed of a foam material.

4. The device of claim 1 wherein the distal end of said membranous section forms a liner for the cavity of said tubular section.

5. The device of claim 1 wherein the distal end of said membranous section forms a liner on the outer surface of said tubular section.

6. The device of claim 1 wherein the distal end of said membranous section forms a liner embedded within said tubular section.

7. The device of claim 1 wherein said tubular section is formed of a flexible material.

8. The device of claim 1 wherein the side wall and closed end of said tubular section have a wall thickness in the range of between about 0.125 and 0.5 inches.

9. The device of claim 1 wherein said tubular section is formed of a nonelastic material.

10. The device of claim 1 wherein said tubular section is formed of a material which can allow said tubular section to be everted.

11. The device of claim 1 wherein said tubular section has at least one groove on the interior side wall of said tubular section which can allow passage of air from the cavity to said impermeable membranous section.

12. The device of claim 1 wherein the said tubular section has stimulating surfaces disposed on the interior of the side wall of said tubular section.

13. The device of claim 12 wherein the stimulating surfaces are selected from the group of patches, rings and lines of hair-like strands.

14. The device of claim 1 wherein the outer surface of the tubular section includes the anatomical features of a male organ.

15. The device of claim 1 wherein the outer surface of the side wall of the tubular section has stimulating surfaces.

16. A device for shielding the male organ, comprising:
   a) a tubular section having a side wall, a closed end and an open end, which forms a cavity for receiving the male organ through said open end and wherein the side wall and closed end of said tubular section have a wall thickness in the range of between about 0.125 and 0.5 inches; and
   b) an impermeable, flexible membranous section having a membrane, wherein said membranous section has a wall thickness that is less than the thickness of the side wall of the tubular section and is essentially cylindrical in shape having a proximal end and a distal end, wherein said distal end is circumferentially attached about the open end of said tubular section and wherein said proximal end has means for securing said membrane to the base of the male organ.

\* \* \* \* \*